United States Patent
Geistert et al.

(10) Patent No.: US 6,287,303 B1
(45) Date of Patent: Sep. 11, 2001

(54) ABLATION INSTRUMENT FOR INTRACARDIAC TREATMENTS

(75) Inventors: Wolfgang Geistert, Rheinfelden-Herten; Markus Bothur, Wittlingen, both of (DE)

(73) Assignee: Sulzer Osypka GmbH, Grenzach-Wyhlen (DE)

(*) Notice: Subject to any disclaimer, the term of this patent is extended or adjusted under 35 U.S.C. 154(b) by 0 days.

(21) Appl. No.: 09/319,300

(22) PCT Filed: Nov. 21, 1997

(86) PCT No.: PCT/EP97/06525

§ 371 Date: Jun. 3, 1999

§ 102(e) Date: Jun. 3, 1999

(87) PCT Pub. No.: WO98/25532

PCT Pub. Date: Jun. 18, 1998

(30) Foreign Application Priority Data

Dec. 12, 1996 (EP) .................................. 96810866

(51) Int. Cl.⁷ .................................... A61B 18/04
(52) U.S. Cl. ................... 606/34; 606/38; 606/41; 606/42; 607/101; 607/102
(58) Field of Search ................... 606/34, 38–42, 606/45, 48, 49, 50; 607/96, 98, 99, 101, 102

(56) References Cited

U.S. PATENT DOCUMENTS

| | | |
|---|---|---|
| 5,383,874 | 1/1995 | Jackson . |
| 5,542,916 | 8/1996 | Hirsch . |
| 6,106,522 * | 8/2000 | Fleischman et al. .................. 606/41 |

FOREIGN PATENT DOCUMENTS

| | | |
|---|---|---|
| WO 91/16859 | 11/1991 | (WO) . |
| WO 93/20770 | 10/1993 | (WO) . |
| WO 94/10922 | 5/1994 | (WO) . |
| WO 96/00528 | 1/1996 | (WO) . |

* cited by examiner

Primary Examiner—Linda C. M. Dvorak
Assistant Examiner—R. Kearney
(74) Attorney, Agent, or Firm—Townsend and Townsend and Crew LLP

(57) ABSTRACT

The invention relates to an ablation apparatus for intracardiac treatments which comprises a high-frequency source whose power output is controlled in a power-or temperature-controlled mode. Ablation catheters which each comprise at least one energy-emitting pole can be used with the apparatus, the or each pole comprising at least one temperature sensor for measuring the temperature of a tissue. The temperature sensors of the poles are either thermistors or thermocouples. The instrument further comprises a sensor-detection system and corresponding devices by means of which the power output can be automatically regulated such that the power is regulated according to the actual catheter type. To that end, it is not necessary to use a specially coded catheter and no special manual operations are necessary for adjusting the catheter type.

17 Claims, No Drawings

ABLATION INSTRUMENT FOR INTRACARDIAC TREATMENTS

This application is a 371 of PCT/E97/06525 Nov. 21, 1997.

BACKGROUND OF THE INVENTION

1. Field of the Invention

The invention relates to an ablation apparatus for intracardial heart treatments with a high-frequency energy source (RF source for short) and to a method for operating the apparatus.

2. Description of the Prior Art

During the ablation, tissue layers in the heart are denatured by means of a flexible catheter in order to eliminate disturbances of the stimulus conduction system. Disturbances of this kind manifest themselves as heart arrhythmias (e.g. tachycardia). The disturbing stimulus conductors are localized and then intentionally interrupted using the ablation catheter. The tissue lesion carried out for the interruption is performed with the help of high frequency alternating currents of an RF source. The power output of the RF source is adjusted by means of a temperature regulation in such a manner that the cells are necrotised, but that the cellular composition (the tissue) is not destroyed and that no coagulation takes place at the pole giving off the energy.

Ablation apparatuses are composed of an apparatus part which contains the RF source and at least one catheter which is connected to the RF source and has one or more poles which give off energy.

Different types of catheters are used, for example those which differ in the temperature sensors at the poles. These sensors can be thermistors or thermoelements.

As a result of inhomogeneities in the heat conduction, a temperature distribution with different temperatures can arise on the pole. The temperature sensor measures an average temperature and thus local overheatings can arise on the pole. The temperature relationships on the pole can be better measured with a plurality of temperature sensors.

The pole can be assembled from a plurality of separate segments, which are all connected to the same RF source and each of which contains a separate temperature sensor. The ablation can also be carried out using two catheters which are separate but connected to the same RF source and act on the same tissue location. In this case the poles of the two catheters represent two segments of a common pole or else two opposite poles.

Catheters are also known which have no temperature sensors.

There is also a large variety of catheters which differ with respect to different sensor types (when there is a sensor present) and/or which differ with respect to the number of sensors, which can also be zero.

In known ablation apparatuses (e.g. the Cordis-Webster/Stockert "EP shuttle") the catheter type must be set manually. This manual setting is an action which must be performed specially by the user and which can lead to an error in the operation as a result of a confusion of the catheters.

U.S. Pat. No. 5,383,874 describes catheters with codings which make the type of the catheter recognisable by the apparatus. These catheters can however be used only with apparatuses which are capable of deciphering this coding. Conversely, only catheters which contain this coding can be used with these apparatuses.

SUMMARY OF THE INVENTION

The object of the invention is to provide an ablation apparatus which permits a free choice from a wide selection of catheter types, wherein operating errors should be largely avoidable in cases which are possible in practice.

The ablation apparatus for intracardial heart treatments has an RF source, the power output of which takes place in a regulated manner in a power or temperature regulated mode. Ablation catheters, each of which comprises at least one energy output pole can be used with the apparatus, with it being possible for the or each pole to contain at least one temperature sensor for the measurement of a tissue temperature. The temperature sensors of the poles are either thermistors or thermoelements. A sensor recognition and corresponding means are provided, as a result of which the regulation for the power output can be automatically set in such a manner that the carrying out of the power regulation corresponds to the current catheter type. In this situation it is not necessary for the catheter to have a special coding and no special manual acts of the user are required for setting the type of catheter.

DETAILED DESCRIPTION OF THE PREFERRED EXEMPLARY EMBODIMENTS

The ablation apparatus has a sensor recognition and corresponding means, as a result of which the measurement values of current sensors are automatically used for the regulation of the power output. A switchover to the type of catheter which is connected is automatically and reliably done through the sensor recognition.

Measurement circuits for the thermistor or the thermoelement respectively are designed for the automatic recognition as follows: 1. The thermistor measurement circuit can distinguish the states "open", "short circuit" and "valid sensor". 2. The thermoelement measurement circuit can distinguish the states "open" and "not open" as well as advantageously "plausible temperature value". (The "short circuit" state can not be distinguished by the thermoelement measurement circuit since a thermoelement which has the same temperature as an associated comparison location appears as a short circuit.)

A recognition algorithm of the sensor recognition operates as follows: 1. If the state "open" is detected by the currently active measurement circuit the thermistor measurement circuit is always switched on. 2. If the thermistor measurement circuit detects a "valid sensor", then the result of the automatic recognition is "thermistor". 3. If the thermistor measurement circuit detects a short circuit, the result of the automatic recognition is "thermoelement". (The thermistor measurement circuit then can be deactivated and the thermoelement measurement circuit activated.)

The sensor type recognition will be described in somewhat more detail in the following:

The ablation apparatus contains two measurement circuits for the determination of the temperature present at the thermistor or thermoelement respectively. These measurement circuits can be activated individually. The automatic recognition can also be carried out using them in that resistances between the hook-up connectors of the sensors are determined. "States" of the sensors can be associated with the measured resistances:

a) The thermistor measurement circuit can distinguish the states "open", "short circuit" and "valid sensor". "Open" is recognized when a certain resistance value is exceeded, i.e. when a temperature derived from the measurement is correspondingly dropped below. "Short circuit" is recognised when a certain resistance value is dropped below, i.e. when a temperature derived from the measurement is correspondingly exceeded.

"Valid sensor" is recognized when the resistance measured lies between the values beyond which "open" and "short circuit" respectively are recognized, i.e. when a temperature derived from the measurement lies in a predetermined range.

b) The thermoelement measurement circuit can distinguish the states "open" and "not open" as well as advantageously "plausible temperature value". The "short circuit" state can not be determined directly by the thermoelement measurement circuit since a thermoelement which has the same temperature as an associated comparison location appears as a short circuit. The "open" state can be recognized through a suitably designed circuit for example in that "pull-up" or "pull-down" resistances respectively "pull" towards a given value which is not accepted by the circuit which is in operation with a thermoelement connected.

The state "plausible temperature value" is recognised when a temperature derived from the measurement lies in a predetermined validity range. In this situation the sensor operates as follows:

1. If the momentarily active measurement circuit recognized the "open" state, the thermistor measurement circuit is always switched on.
2. If the thermistor measurement circuit recognized the "open" state, then the result of the automatic recognition is "open". Consequently only power regulation instead of temperature regulation is possible.
3. If the thermistor measurement circuit recognized a "valid sensor", then the result of the automatic recognition is "thermistor". The thermistor measurement circuit thus remains activated and a temperature regulated ablation is possible.
4. If the thermistor measurement circuit recognized a short circuit, then the result of the automatic recognition is "thermoelement".The thermistor measurement circuit is thereupon deactivated and the thermoelement measurement circuit is activated.
5. If the thermoelement measurement circuit recognized a state other than "open", then the temperature regulated ablation is possible.

In addition to the sensor type recognition, means are advantageously provided by means of which one or more tests can be carried out which are concerned with whether the connected sensors are providing plausible temperature values: The temperature values should lie in the expected ranges. When catheters with thermoelements are used, it can where appropriate also be determined using tests whether comparison points of the thermoelements are also providing plausible values.

Additional means are advantageous by means of which the measurement circuit for the temperature measurement can be calibrated and tested.

For the observation of the thermal effect on the tissue arising during the ablation, one or several of them can be provided on the tissue as a temperature sensor. It is however also possible that no sensor is present or that a sensor is defective.

Thus in the automatic sensor recognition, means are advantageous by means of which the number of connected sensors can automatically be determined and by means of which the ablation apparatus can be set accordingly.

Furthermore, means are advantageous with the use of which a monitoring of the start phase can be carried out as a result of the information from the sensor recognition. Through a monitoring of this kind it is to be prevented that the ablation apparatus inadvertently starts in a power regulated mode instead of in the temperature regulated mode in the event that no sensors are detected. This is a case of an "intelligent start" of the apparatus in accordance with the invention. It is carried out by the following algorithm, which is associated with the named monitoring.

As soon as a catheter with a temperature sensor is connected and this is recognized, the monitoring is automatically activated. If now an RF output is started with a temperature sensor connected, then this proceeds without further operating actions, i.e. an RF output is started in the temperature regulated mode. If, however, a catheter without a temperature sensor was connected in the meantime, or if the temperature measurement circuit is open due to a defective sensor or an intermittent contact, then a query results as to whether the RF output should actually be done in a power regulated mode. If this is negated, then the process is interrupted (i.e. the RF output is not started) and the monitoring remains active. If it is affirmed, however, the monitoring is deactivated. The RF output is now started immediately in the power regulated mode or it can be started by means of a further push of a button. From now on, further RF outputs can be started in the power regulated mode without the start having to be confirmed in each case until a catheter with a temperature sensor is again connected. The monitoring is advantageously activated after switching on the apparatus so that a catheter with a temperature sensor is always requested at the beginning.

In the following a few further supplementary explanations are made on the algorithm concerning the "intelligent start".

When the measurement circuits report the "open" state, the algorithm described in the following prevents an inadvertent start in the power regulated mode while simultaneously minimising the operating action. This start blocking comprises the following items:

1. As soon as a catheter with a temperature sensor is connected and this is recognized, the monitoring is automatically activated. If now an RF output is started with a temperature sensor connected, then this proceeds without further actions on the part of the user, i.e. an RF output is started in the temperature regulated mode.
2. If, however, a catheter without a temperature sensor was connected in the mean time or the temperature measurement circuit is open due to a defective sensor or an intermittent contact, then a query results as to whether the RF output should actually be done in a power regulated mode. If this is negated, then the process is interrupted (i.e. the RF output is not started) and the monitoring remains active. If it is affirmed, however, the monitoring is deactivated. The RF output is now started immediately in the power regulated mode or it can be started by means of a further push of a button.
3. From now on, further RF outputs can be started in the power regulated mode without the start having to be confirmed in each case until a catheter with a temperature sensor is again connected.

The monitoring is advantageously activated after switching on the apparatus so that a catheter with a temperature sensor is always requested at the beginning.

Catheters with a plurality of sensors and, under certain conditions, with a plurality of ablation poles are also known. In this event the sensor recognition system or a plurality of sensor recognition systems can be used to determine the number of sensors connected and to set the regulation or the mode of operation of the ablation apparatus accordingly.

For this, measurement circuits for thermistors and/or thermoelements can be associated with the possible sensor connections. In order to reduce the number of measurement circuits a group of possible sensor connections can in each case be associated with one measurement circuit, which can be connected sequentially via a multiplexer to the connections of a group.

Various algorithms are conceivable for setting the modes of operation: For example the values of all recognized temperature sensors can automatically be fed to the regulator when an ablation catheter with one pole is connected. If ablation catheters with a plurality of ablation poles are connected, a logic circuit can automatically associate certain sensors with each pole.

What is claimed is:

1. An ablation apparatus for intracardial heart treatments, the apparatus comprising:
   an RF source, wherein the power output of the RF source is regulated in a power or temperature regulated mode;
   at least one ablation catheter that may be connected to the RF source and that comprises at least one energy output pole, wherein the at least one energy output pole may contain at least one temperature sensor and the temperature sensors of the poles are one of either thermistors or thermoelements; and
   a sensor recognition system configured such that regulation of power output may be automatically set in such a manner that carrying out of the power regulation corresponds to the type of at least one ablation catheter without the need for the catheter to have a special coding and further configured such that special manual actions of a user are not required for setting of the type of at least one ablation catheter;
   wherein the sensor recognition system comprises a sensor type recognition system through which there may be determined whether the temperature sensors of the poles are thermistors or thermoelements.

2. An ablation apparatus in accordance with claim 1 further comprising means for carrying out at least one test that is intended to determine whether connected sensors yield plausible temperature values.

3. An ablation apparatus in accordance with claim 2 wherein the means for carrying out at least one test may provide comparison points that yield plausible temperature values for the thermoelements.

4. An ablation apparatus in accordance with claim 1 further comprising means for calibrating and testing measurement circuits for the temperature measurements.

5. An ablation apparatus in accordance with claim 1 further comprising means for monitoring of a start phase so that the monitoring may prevent an unintentional start in a power regulated mode.

6. An ablation apparatus in accordance with claim 1 further comprising means for determination of the number of connected sensors and a plurality of measurement circuits, wherein the measurement circuits are switched via one or more multiplexers to connections at which connections a thermo-sensor is to be expected, and wherein the ablation apparatus further comprises means for setting the mode of operation of the apparatus to the presence of sensors and the number of sensors.

7. An ablation apparatus for intracardial heart treatments, the apparatus comprising:
   an RF source, wherein the power output of the RF source is regulated in a power or temperature regulated mode;
   at least one ablation catheter that may be connected to the RF source and that comprises at least one energy output pole, wherein the at least one energy output pole may contain at least one temperature sensor and the temperature sensors of the poles are one of either thermistors or thermoelements; and
   a sensor recognition system configured such that regulation of power output may be automatically set in such a manner that carrying out of the power regulation corresponds to the type of at least one ablation catheter without the need for the catheter to have a special coding and further configured such that special manual actions of a user are not required for setting of the type of at least one ablation catheter;
   wherein the sensor recognition system comprises means for determining the number of connected sensors.

8. An ablation apparatus in accordance with claim 7 further comprising means for carrying out at least one test that is intended to determine whether connected sensors yield plausible temperature values.

9. An ablation apparatus in accordance with claim 7 wherein the means for carrying out at least one test may provide comparison points that yield plausible temperature values for the thermoelements.

10. An ablation apparatus in accordance with claim 7 further comprising means for calibrating and testing measurement circuits for the temperature measurements.

11. An ablation apparatus in accordance with claim 7 further comprising means for monitoring of a start phase so that the monitoring may prevent an unintentional start in a power regulated mode.

12. An ablation apparatus in accordance with claim 7 further the comprising means for determination of the number of connected sensors and a plurality of measurement circuits, wherein the measurement circuits are switched via one or more multiplexers to connections at which connections a thermo-sensor is to be expected, and wherein the ablation apparatus further comprises means for setting the mode of operation of the apparatus to the presence of sensors and the number of sensors.

13. A method for operation of an ablation apparatus, the method comprising providing:
   an ablation apparatus for intracardial heart treatments, the apparatus comprising:
      an RF source, wherein the power output of the RF source is regulated in a power or temperature regulated mode; and
   at least one ablation catheter that may be connected to the RF source and that comprises at least one energy output pole, wherein the at least one energy output pole may contain at least one temperature sensor and the temperature sensors of the poles are one of either thermistors or thermoelements;
   providing the ablation apparatus with two activatable sensor measurement circuits that are respectively associated with a thermistor and a thermoelement;
   supplying data on the presence of sensors of a connected catheter with the two activatable sensor measurement circuits;
   supplying data on the states of the sensors in a case of a presence of a sensor;
   deciding as a result of the determined states, with a recognition algorithm, whether a sensor measurement circuit is to be activated and, if so, which sensor measurement circuit; and
   switching on the power or temperature regulated mode accordingly.

14. A method in accordance with claim 13, wherein states "open," "short circuit" and "valid sensor" are distinguished by the thermistor measurement circuit and states "open" and "not open" are distinguished by the thermoelement measurement circuit, wherein the thermistor measurement circuit is activated when the state "open" is determined, and wherein when the thermistor measurement circuit is already activated and the state "short circuit" is determined, the thermoelement measurement circuit is activated.

15. The method in accordance with claim 13 further comprising monitoring of a start phase, wherein data on the presence of sensors of a connected catheter are supplied by at least one measurement circuit, wherein a decision is made by a recognition algorithm whether the operation is to be in the power or the temperature regulated mode, and wherein in the power regulated mode the start blocking is not deactivated until after a positive reply to a query.

16. A method in accordance with claim 15 or in the monitoring of the start phase is automatically activated when the ablation apparatus is switched on or when a catheter is recognized as a catheter with temperature sensors when being connected.

17. A method in accordance with claim 13 wherein the sensors are automatically associated by a logic circuit with control circuits or the control circuit for the temperature regulation.

* * * * *